United States Patent [19]
Lam et al.

[11] Patent Number: 5,127,032
[45] Date of Patent: * Jun. 30, 1992

[54] MULTI-DIRECTIONAL X-RAY IMAGER

[75] Inventors: Wing-Chee Lam; Veronica Lam, both of Timonium, Md.

[73] Assignee: Johns Hopkins University, Baltimore, Md.

[*] Notice: The portion of the term of this patent subsequent to Dec. 26, 2006 has been disclaimed.

[21] Appl. No.: 394,726

[22] Filed: Aug. 15, 1989

Related U.S. Application Data

[63] Continuation-in-part of Ser. No. 128,224, Dec. 3, 1987, Pat. No. 4,890,313.

[51] Int. Cl.⁵ ............................................. H01J 31/50
[52] U.S. Cl. ............................... 378/189; 378/65; 378/190
[58] Field of Search .................... 378/57, 65, 189, 167, 378/181, 190; 250/458.1

[56] References Cited

U.S. PATENT DOCUMENTS

| | | | |
|---|---|---|---|
| 2,508,449 | 5/1950 | Davis | 250/57 |
| 3,434,684 | 3/1969 | Warden | 248/162 |
| 3,560,740 | 2/1971 | Tripp | 250/61 |
| 3,612,867 | 10/1971 | Rabodzei et al. | 250/77 |
| 3,758,723 | 9/1973 | Green | 178/6.8 |
| 4,020,346 | 4/1977 | Dennis | 378/57 |
| 4,052,621 | 10/1977 | Haas | 250/458 |
| 4,233,516 | 11/1980 | Trepte | 250/444 |
| 4,239,969 | 12/1980 | Haas et al. | 378/57 |
| 4,297,580 | 10/1981 | Juner et al. | 378/57 |
| 4,365,344 | 12/1982 | Dornheim | 378/189 |
| 4,379,348 | 4/1983 | Haas et al. | 378/57 |
| 4,454,605 | 6/1984 | DeLucia | 378/57 |
| 4,890,313 | 12/1989 | Lam et al. | 378/189 |

*Primary Examiner*—Janice A. Howell
*Assistant Examiner*—David P. Porta
*Attorney, Agent, or Firm*—Banner, Birch, McKie & Beckett

[57] ABSTRACT

A multi-directional x-ray imager for use with an isocentric therapy x-ray machine having a rotatable x-ray source. The imager has a fluorescence screen which emits light when excited by x-rays from the source and an imaging camera which images the light emission. A rotational joint rotates and aligns the screen relative to a different rotated position of the source relative to the patient. The camera is positioned out of the straight line path of the x-rays passing through the screen, and a deflecting mirror deflects the emitted light to the camera. The mirror includes a thin sheet of reflective material, such as aluminized plastic, to prevent the x-rays impinging thereon from scattering to the (solid state video) camera.

62 Claims, 9 Drawing Sheets

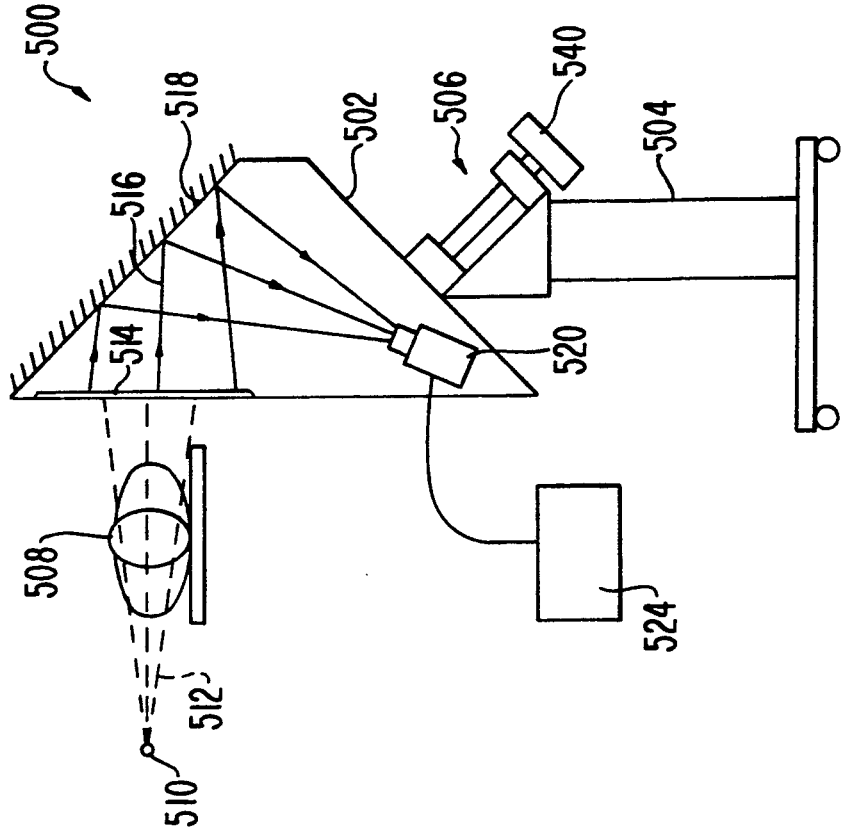
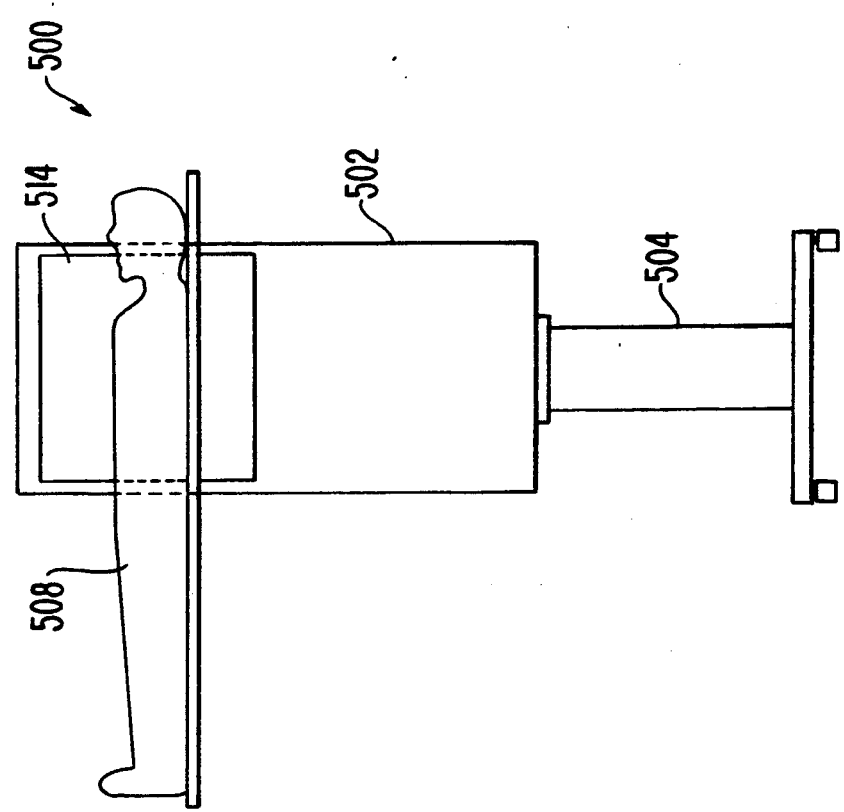

MULTI-DIRECTIONAL X-RAY IMAGER

BACKGROUND OF THE INVENTION

This is a continuation-in-part of copending application Ser. No. 07/128,224, filed Dec. 3, 1987, which issued Dec. 26, 1989 as U.S. Pat. No. 4,890,313, and whose entire contents are hereby incorporated by reference.

This invention relates to therapeutic systems for indicating alignment of x-ray beams with patient areas.

Many types of apparatus have been used in locational association with x-ray equipment, including those disclosed in the following U.S. patents, each of whose entire contents are hereby incorporated by reference: U.S. Pat. No. 2,508,449 to Davis, which shows an apparatus that can be pivoted one hundred and eighty degrees for vertical or horizontal fluoroscopic use; U.S. Pat. No. 3,612,867 to Rabodzei, which shows an angle-adjustable x-ray/TV apparatus with tiltable reflection element; U.S. Pat. No. 3,758,723 to Green, which shows an x-ray/TV system with an angled mirror; and 4,233,516 to Trepte, which shows a fluoroscopic apparatus adjustable to horizontal and vertical positions.

The purpose of the imager of the present invention is to take x-ray images of patients under treatment to make sure that the treatment region is correctly aligned with the x-ray field. To cover the size of the x-ray images, an x-ray imager for a rotating gantry of a radiotherapy x-ray machine has to have a large fluorescence screen (about fifty by fifty centimeters) and a mirror of about the same size and these have to be arranged at a precise angle to each other. It is very difficult and very costly to build such an imager which is also retractable, and retractability is very important. To take an image, the imager has to extend out and to a position opposite to the x-ray source behind the patient. If the imager does not retract from its extended position, it interferes with the technical setting up of the patient for treatment.

SUMMARY AND ADVANTAGES OF THE INVENTION

1. Detection of geometric treatment errors. Since a large portion of patient treatments are performed with the x-ray pointing either vertically or horizontally, a guidance image can be obtained at the same time as the treatment, using principles of this imager. From the obtained position of the anatomic structures, it can be determined whether there is any misalignment of the x-ray field with respect to the target volume. If an error is detected, the patient setup can be adjusted correctly before the full radiation dosage is given. In case treatment is not performed with the x-ray pointing either vertically or horizontally, the patient can still be imaged in these two directions as "reference" position with a small dosage of x-rays. The patient can then be treated at other desired angles, but the reference images can be used in collaboration with similar images taken with other diagnostic machines (such as radiotherapy simulators and computed tomography scanners) which can image the patient in the two "reference" directions as well as in the treatment direction.

2. Documentation of treatment. The images obtained by the imager can be recorded on magnetic storage media or optical storage media, and provide a permanent record of how the treatment was carried out.

3. Versatility in mechanical design. The imager is relatively compact and easy and quick to position. It has only one imaging arm, but it can be rotated to image the patient with x-rays impinging in a selected one of two different directions (horizontal and vertically downward). It is well supported but lightweight, and convenient to use and can be manufactured at relatively low cost.

4. Simplicity. Mechanically, the invention provides one rotating joint connecting two boxes together, or one box and a counterweight. The electro-optical components are few and simple to install and service.

In consonance with the above, ramifications of the invention can be stated in other ways.

Correct patient setup for radiation therapy treatment relies on the reference anatomic landmarks. This imager can obtain images of such localization landmarks and convert them into electronic signals. By using a video digitizer, the image can be digitized into a computer in real-time. The image can then be enhanced to bring out low contrast objects using digital image pressing technique. Thus, it facilitates the comparison of treatment position with the reference position of the patient. From this comparison, any error detected can be corrected before the full dose is delivered.

The video image can be stored in magnetic storage device or optical storage devices for documentation of treatments. It saves storage space compared with the conventional means of using photographic film.

From the brightness of the image and the time of irradiation, the dose delivered to the patient can be calculated. Thus the invention provides an independent method to monitor the dose delivered to the patient.

The system can be extended to cover more angles if (1) in the base of the lower box is made into a cylindrical sector and moves on a complementary circular track, (2) the screen can be tilted at a larger angle to the mirror as will be shown, or (3) a rotational joint-counterweight design is used.

The above and other objects and advantages of this invention will become more readily apparent from the following description, including the drawings in which like reference numerals refer to like parts.

BRIEF DESCRIPTION OF THE DRAWINGS

FIG. 5a is a view taken at line 5a—5a in FIG. 3a.

FIG. 5b is a view taken at line 5b—5b in FIG. 4a.

FIG. 7 is an enlarged elevational diagram of a mirror positioner mechanism for use in conjunction with the smaller mirror shown in FIG. 4a.

FIG. 10 is a front elevational view of another imaging system of the present invention arranged for horizontal irradiation; the x-ray source is shown in front of the patient and the imager behind him.

FIG. 11 is a side elevational view of the imaging system of FIG. 10.

DETAILED DESCRIPTION OF PREFERRED EMBODIMENTS OF THE INVENTION

Figure 1:
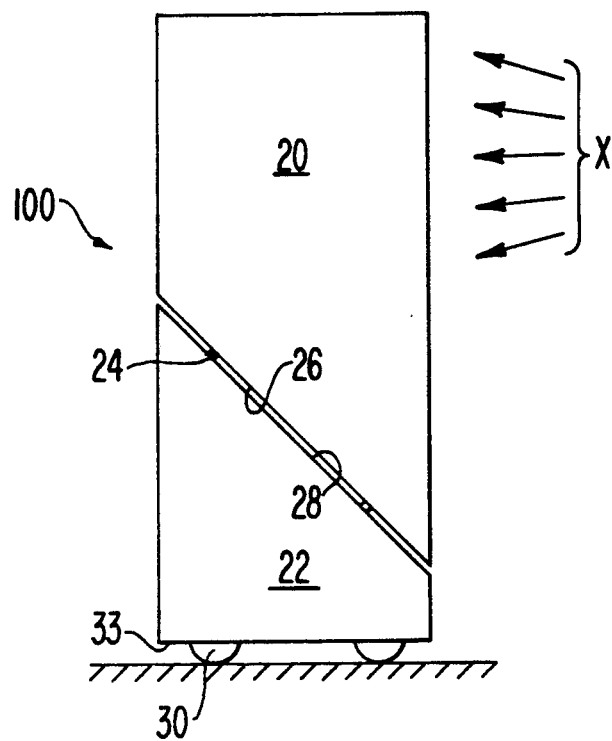
FIG. 1 is an elevational view of the exterior of either a first or a second embodiment of an imager system according to this invention, the appearance being the same, arranged for use observing alignment in horizontal irradiation (arrows) of a patient (not shown).
Figure 2:
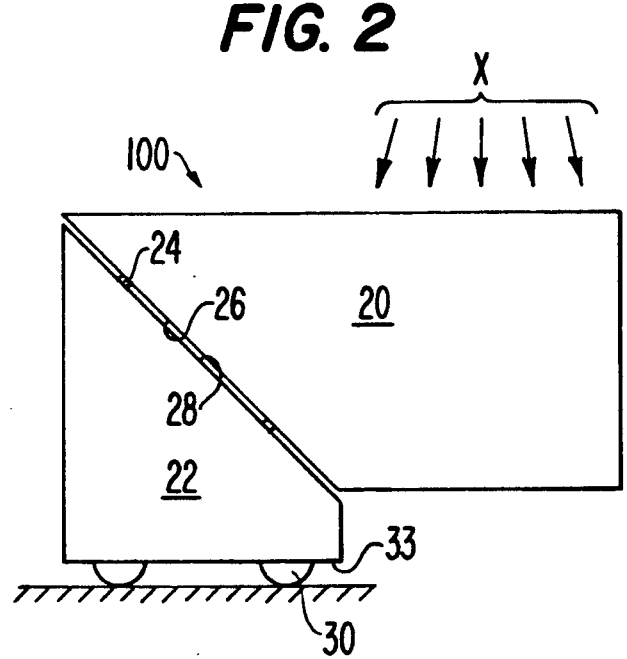
FIG. 2 is an elevational view typical of the first or second embodiments arranged for use observing alignment in vertically downward irradiation of a patient.

FIGS. 1 and 2 show the exterior of the housing means or cabinet of embodiment 100 of a multi-directional x-ray imager according to this invention. The exterior of embodiment 200 looks the same. In these and other figures x-rays are indicated by arrows at "x". The invention includes, depending on the embodiment, either three or four electro-optical components, to be described, mounted inside two light-tight boxes 20, 22 connected together by a rotational joint 24, preferably light-tight in itself, and formed at a respective bevelled end of each box. Each of the bevel ends 26, 28 lies at a forty-five degree angle to the length of a box 20, 22 as does the rotational joint 24. The lower box 22 is always vertical and may have rollers 30 on the lower end thereof. When the upper box 20 is rotated one hundred and eighty degrees from the FIG. 1 upper box vertical orientation it assumes the FIG. 2 orientation, horizontally perpendicular to the lower box 22. It may snap precisely into the orientation of either FIG. 1 or FIG. 2, retained by a typical plunger and socket spring detent, described later. Inside the boxes, electro-optical components are arranged to define either of two embodiments, held as by brackets 19 indicated in FIG. 3a, for example.

Figure 3A:
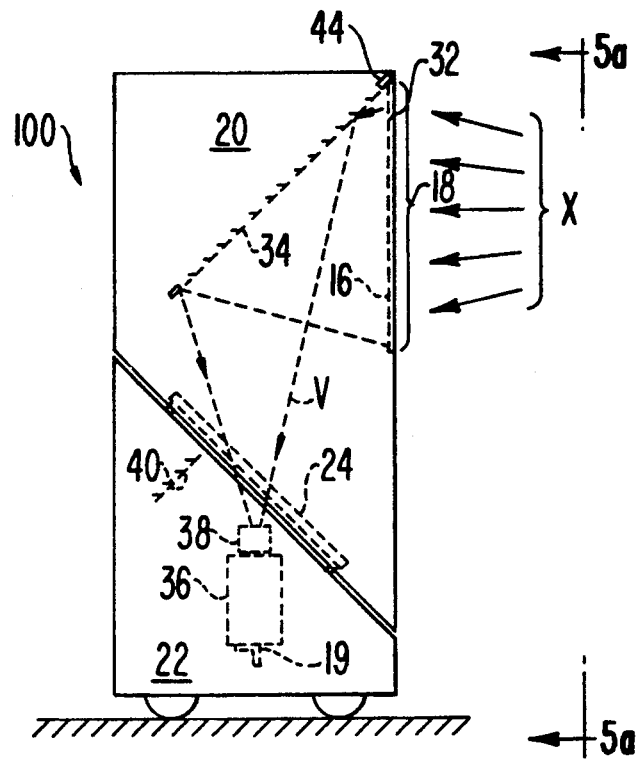
FIG. 3a is an elevational view diagramming in phantom lines the interior of the first embodiment arranged for use in observing alignment in horizontal irradiation procedures.
Figure 3B:
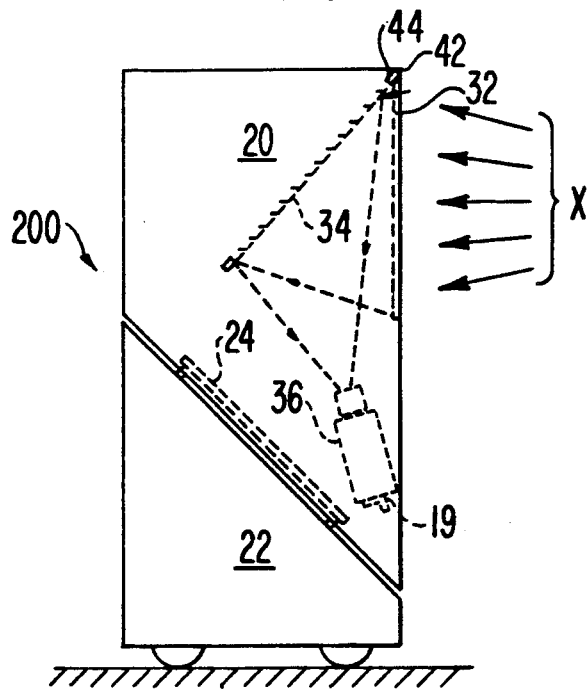
FIG. 3b is a view similar to that of FIG. 3a but diagramming similarly the interior of the second embodiment arranged for use in observing alignment in horizontal irradiation.
Figure 4A:
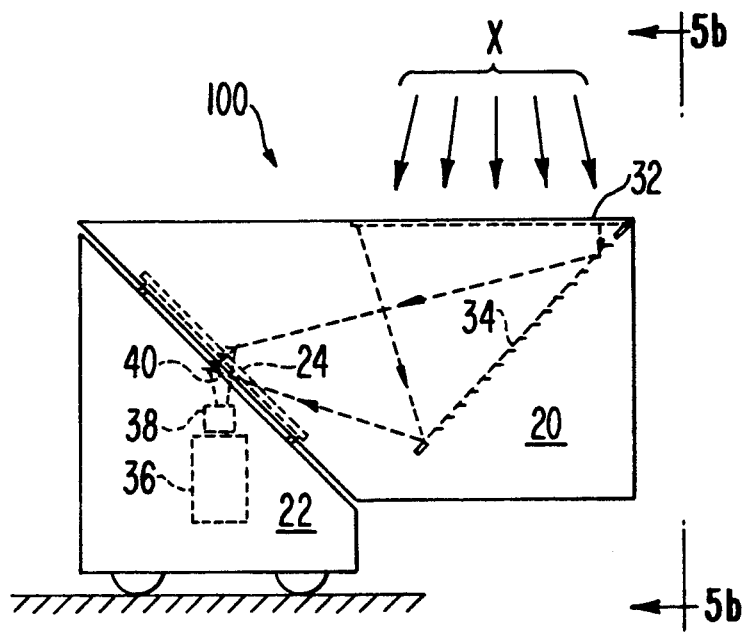
FIG. 4a is an elevational view diagramming the interior of the first embodiment arranged for use observing alignment in vertically downward irradiation procedures.
Figure 4B:
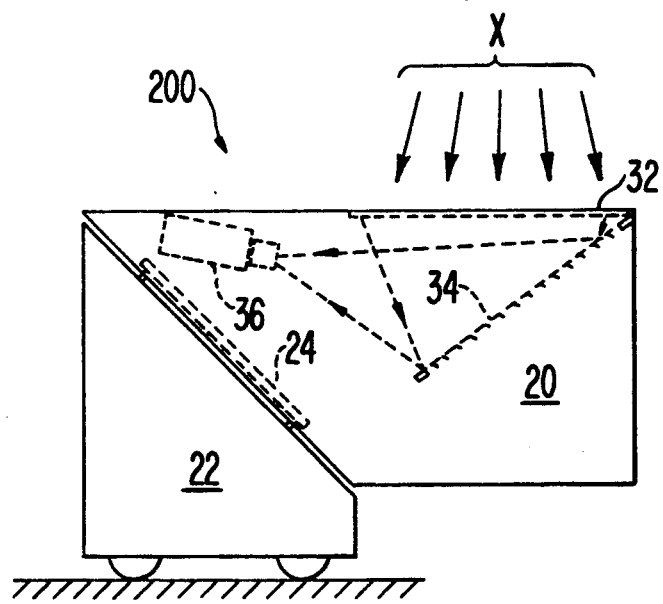
FIG. 4b is a view similar to FIG. 4a and shows the interior of the second embodiment arranged for use observing alignment in vertically downward irradiation procedures.

FIGS. 3a and 3b show, respectively, the two embodiments 100 and 200, with the upper box 20 upright on the lower box 22 in vertical orientation, for monitoring horizontal irradiation (arrows X). FIGS. 4a and 4b show, respectively, the embodiments 100 and 200 with the upper box 20 at ninety degrees to the lower box 22, in horizontal orientation, for monitoring vertical irradiation (arrows X).

FIGS. 3a and 4a show that in embodiment 100 of the imager, a fluorescence screen 32 which covers an opening or window 18, covered by a metal plate 16 such as, for example, a two millimeter thick aluminum plate, shown in FIG. 3a but typical of all views of box 20, and first diagonal mirror 34, are mounted in the upper box 20 and a video camera 36 with conventional focussing optics 38 and a second, retractable, diagonal mirror 40 to relay the beam in the second orientation are mounted in the lower box 22. Direction of retraction of mirror 40, out of the field of view "V" of the video camera, may be in the plane of mirror 40, or, as indicated in FIG. 3a, it may be retracted in any other suitable direction. Embodiment 100 provides more room for shielding around the camera to protect it from scattered x-rays than does embodiment 200.

FIGS. 3b and 4b show how in embodiment 200 all the optical and electro-mechanical components (fluorescence screen 32, diagonal mirror 34 and video camera 36) are located in the upper box 20. A second diagonal mirror is unnecessary in embodiment 200, since there is no relative rotation of components when one box is rotated relative to the other. The amount of space in embodiment 100 for shielding around the video camera 36 is limited, and embodiment 200 is better used in therapy machines that do not generate a large amounts of scattered x-rays.

Figure 5A:
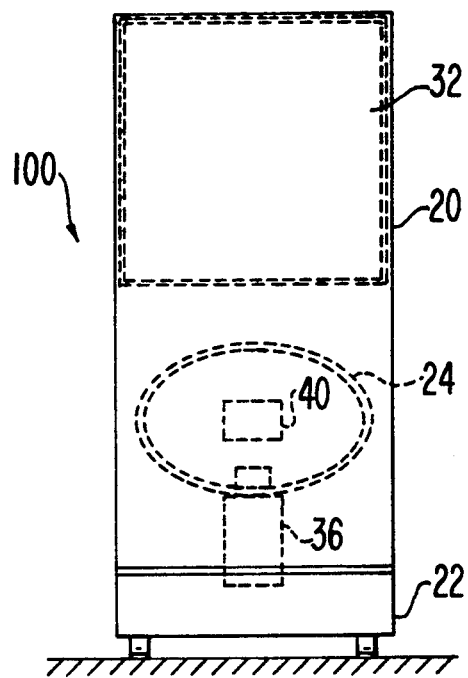

FIG. 5a shows the front view of embodiment 100 with the boxes 20, 22 oriented for receiving horizontal irradiation, rotational joint 24, fluorescence screen 32, video camera 36 and second diagonal mirror 40, which would be retracted in this mode of operation.

Figure 5B:
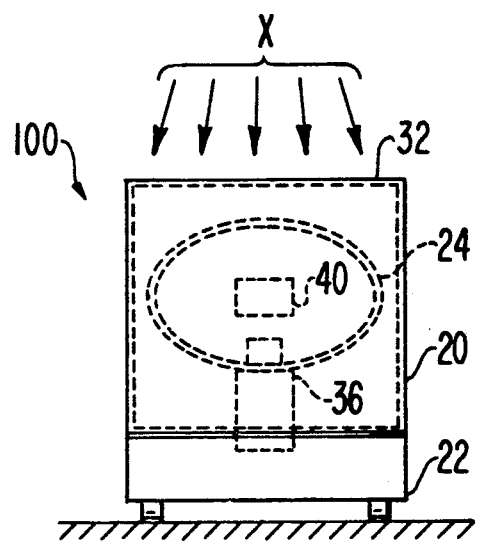

FIG. 5b shows the front view of embodiment 100 with the boxes 20, 22 oriented for receiving vertical irradiation, rotational joint 24, fluorescence screen 32, video camera 36 and diagonal mirror 40, which in this view would be in the video camera field of view.

Figure 6A:
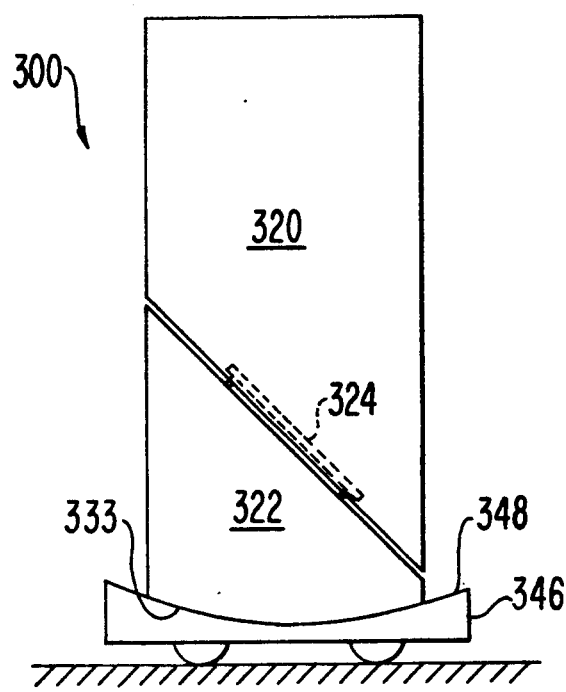
FIG. 6a is an elevational view of a third embodiment of the present invention.

FIG. 6a shows in embodiment 300 an arrangement permitting angularly adjusting with respect to the vertical an entire imager system represented by the boxes 320, 322 and otherwise similar to either of the embodiments shown above, using a separate base 346 that has a concave upper surface 348 of cylindrical contour with axis horizontal. The bottom 333 of the lower box 322 may have a matching convex contour so that the angular relation of box and base is adjustable at the interface. This provision can supplement but not interfere with the rotary joint 324.

Figure 6B:
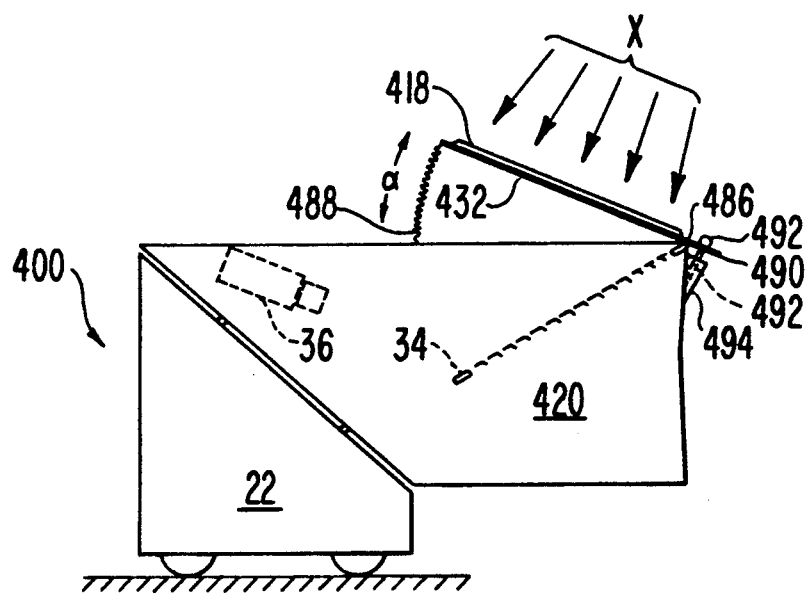
FIG. 6b is an elevational view of a fourth embodiment.

FIG. 6b shows a similar embodiment 400, but with an arrangement that permits the fluorescence screen 432 and window 418 to swing out of the surface of the upper box 420 at one end while the other end is hinged at 486 making an adjustable tilt angle between the mirror 34 and the fluorescence screen 432 bigger than the normal setting. This allows the fluorescence screen to better receive the x-rays coming from oblique angles. The image obtained by the camera 36 will appear compressed in the tilted direction because the deflected image of the screen is not normal to the camera. However, by using computer image processing techniques this distortion can be corrected. A bellows 488 preserves light-tightness. A conventional over-center arm 490 can be adjusted by a screen 492 passing through a slot in the arm and threaded at 492' into a block 494 on the end of the upper box 420.

Figure 7:
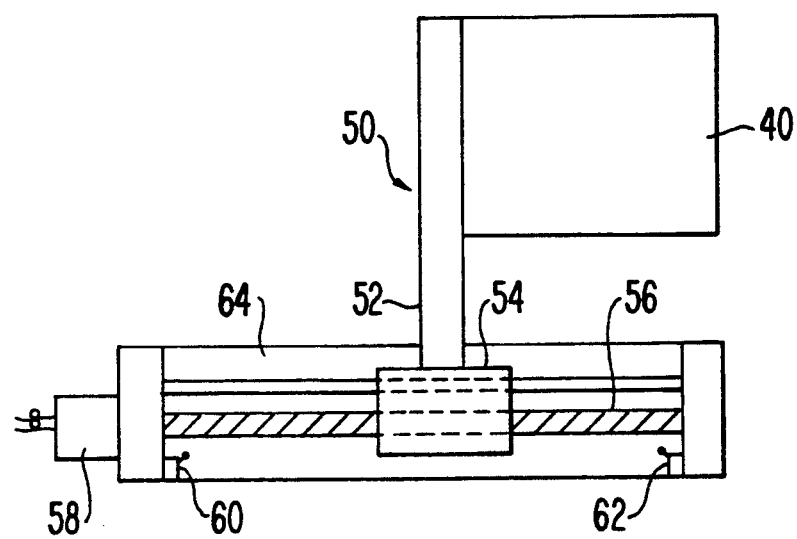

FIG. 7 diagrams a simple positioner 50 for the small mirror 40 (FIGS. 3a, 4a, 5a and 5b) in or out of the video camera field of view of the fluorescence screen, as required. The positioner 50 can be mounted on the lower or fixed box (22, central in the field of view in a plane substantially parallel spaced from the deflection mirror 34, or first diagonal mirror). The mirror may be any ordinary mirror 40 of coated glass or plastic, or may be thin metal. Supported by a pedestal 52, the small mirror 40 is reciprocated by a nut 54 on a screw 56 rotated by an electric motor 58. Conventional limit switches 60, 62 and an on-off motor reverse switch (not shown) may be provided. The nut may be rectangular and guided on the frame 64. The pedestal 52 may be rotated to change the mode of retraction of the mirror 40, which is fixed at the appropriate horizontal axis angle to the pedestal.

Figure 8:
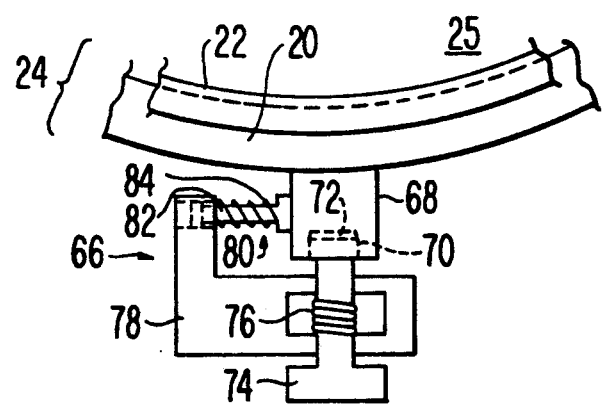
FIG. 8 is an enlarged, fragmentary axial-view diagram of a detent mechanism of the invention.

FIG. 8 shows, in axial view relative to the rotational joint 24, details of a detent mechanism 66 for fixing the rotational relation of the upper box 20 to that of the lower box 22, fragments of which are shown as comprising parts of the rotational joint 24, at the pre-determined positions one hundred and eighty degrees apart in rotation. Preferably two of these are used, respectively on opposite ends of a diameter of the rotational joint 24. A protrusion 68 from one box (for example, 20) at the joint has a socket 70 that is engaged by the bevelled end 72 of a square-section plunger 74 slidably held, against the inward bias of a spring 76, in frame 78 mounted to the other box (for example, 22). A buffer 80 comprising a second plunger 82 captured in the frame slidably at right angles to the first plunger 74 has a spring 84 biasing it to extend, and cushions the stopping action of the detent mechanism in rotationally positioning the boxes. Protrusions 68 may be used to actuate the on-off motor reverse switch (not shown but mentioned in the description of FIG. 7) which controls retraction and extension of the small mirror 40.

Figure 9:
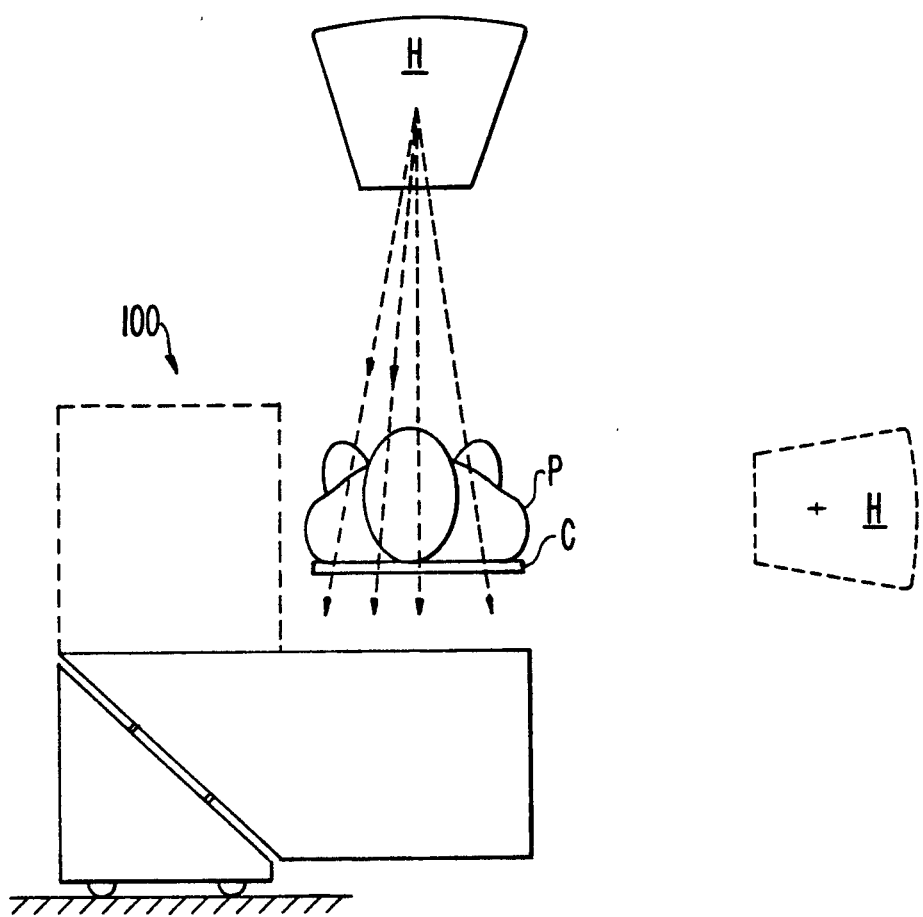
FIG. 9 is an elevational diagram showing an environment of use of apparatus typified by FIGS. 1 and 2, with radiation source and imager shown at two positions (the second position in broken lines) relative to a patient.

FIG. 9 diagrams relations of parts when the system of any embodiment, the first embodiment 100 for example, is in use. A radiation head H may be positioned at either the vertical, or at the horizontal ninety degrees thereto, as shown in (broken lines), relative to a patient P who is supported on a suitable patient support couch C.

The system of this invention can be easily and quickly oriented by rotating the top box, and rolled into position, to align in correspondence with either position. Further details of the components will be noted from the following description.

The fluorescence screen, which may be of conventional material such a zinc sulfide, must be large enough to encompass the treatment field of the therapy machine used, and forms a light-tight seal 42 around the window area, which is the area covered by the fluorescence screen of the upper box. Preferably, the side of the screen facing the x-ray source may be conventionally covered by a thin aluminum or steel or lead plate (not shown) to provide electronic buildup, making the screen more efficient.

The thin deflection mirror or first diagonal mirror 34 is used as noted to locate the video camera 36 out of the path of the x-rays but in position to receive and record images on the fluorescence screen. In embodiment 100, mirror 34 is set at forty-five degrees to the plane of the fluorescence screen 32 and in embodiment 200 is set at about 37.8, for example, depending on the dimension of the upper box 20, degrees to the plane of the fluorescence screen 32 such that the deflected image of the screen is normal to the camera. To prevent scattering of x-rays by the deflection mirror, it is made of a thin reflective sheet of "Mylar" plastic or the like, (0–10 mm aluminized Mylar, for example) stretched over a frame indicated at 44 and taped or otherwise conventionally secured to the frame.

The rotation joint 24 may be any conventional, light-tight ring joint (such as a radial ring flange engaged in a "U"-section ring) that will, as indicated, provide a rotational axis between the long axes of the upper and lower boxes 20, 22 at forty-five degrees to the long axis (vertical axis) of the lower box 22.

In the embodiment 100 the central region 24 of the ring-like joint structure between the boxes may be left open sufficiently not only to provide a thorough optical path from the fluorescence screen to the video camera but also to provide easy access for electrical wiring to the camera. Wiring access can be provided here, also, if needed in the embodiment 200.

Rollers 30 may be of any suitable type, such as casters or flanged wheels to run on tracks. Lead-shielding against scattered x-rays may be provided around the camera and elsewhere in accordance with conventional practice. The lower box has room inside at the bottom for counterbalancing weights, if desired.

Another imaging system of the present invention is illustrated in FIGS. 10–14 generally at 500. Imaging system 500 includes an upper box or housing 502 supported on a stand or carriage 504 and rotatable with respect thereto on a rotation assembly shown generally at 506. The patient as shown at 508 lies on a patient support platform 510 and an x-ray source 509 of an isocentric therapy x-ray machine then can rotate in a circular path with the beam 512 of the source pointing to the center of rotation. These isocentric therapy x-ray machines are well known and are available from a number of manufacturers including Varian Associates, Siemens Corporation, and Philips Medical. The housing 502 then is rotatable about the rotation axis to position the fluorescence screen 514 for receiving the x-rays from the source 510 passing through the patient 508. As the x-rays pass through the fluorescence screen 514, the screen is caused to emit light shown at 516 in FIGS. 11 and 14, and the light then is reflected off of a mirror 518 to an imaging means 520. This imaging means 520 is preferably a video camera, and the video camera is preferably solid state, such as a charge coupled device (CCD) camera, which has a couple of distinct advantages. First, the x-ray illuminated screen (514) often has uneven brightnesses, and the very bright areas can cause "blooming" in the vacuum tube type of video cameras, such as Vidicon cameras. Second, a solid state camera can be easily cooled by means of a Peltier cooling chip. This cooling reduces the electronic noise which effects image quality especially for long exposure modes of operation of the camera. X-rays scattered to the imaging elements of the camera can also produce bright spots in the pictures thereby degrading the quality of the image. Thus, the present invention provides for placing the video camera 520 out of the path of the x-rays by deflecting the emitted light 516 off of the angled mirror 518. To prevent the x-rays from scattering off of the mirror 518 to the video camera 520, the mirror is comprised of a thin sheet of reflective material, such as a one to two millimeters of aluminized material. In other words, the thin mirror reduces the scattering of x-rays to an imaging device which is sensitive to the scattered x-rays.

The video image from the camera 520 can be enhanced by running it through a video digitizer 524, such as is shown in FIG. 11. In this digitizer 524 the video image is converted to a digital image which is run through a peripheral computer which takes the data and performs image enhancement on it. A number of video digitizers are currently available and can be adapted for use herein, and examples thereof are manufactured by Data Translation, Inc. and Matrox, Inc.

Figure 12:
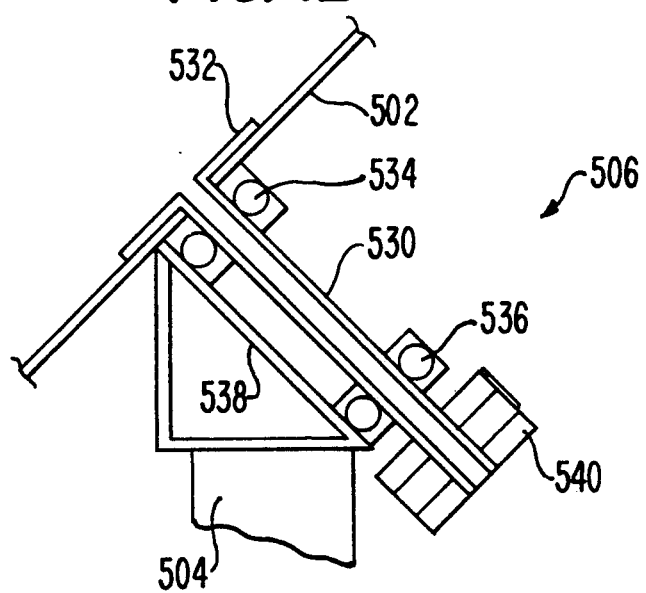
FIG. 12 is an enlarged sectional view of the rotation assembly of the imaging system of FIG. 11.
Figure 14:
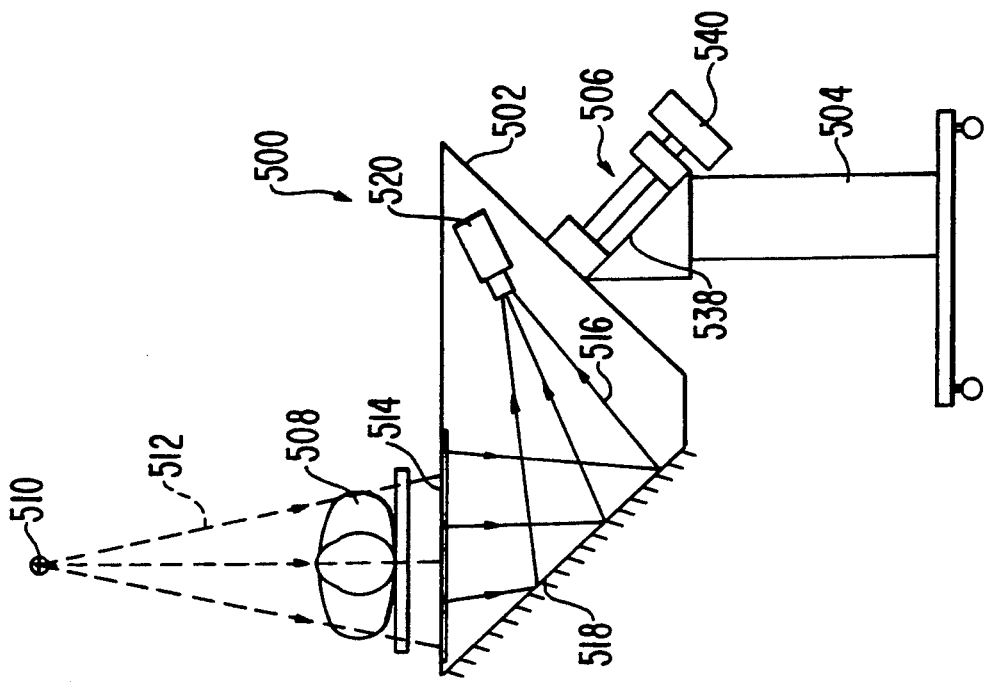
FIG. 14 is a side elevational view of the imaging system of FIG. 13.
Figure 13:
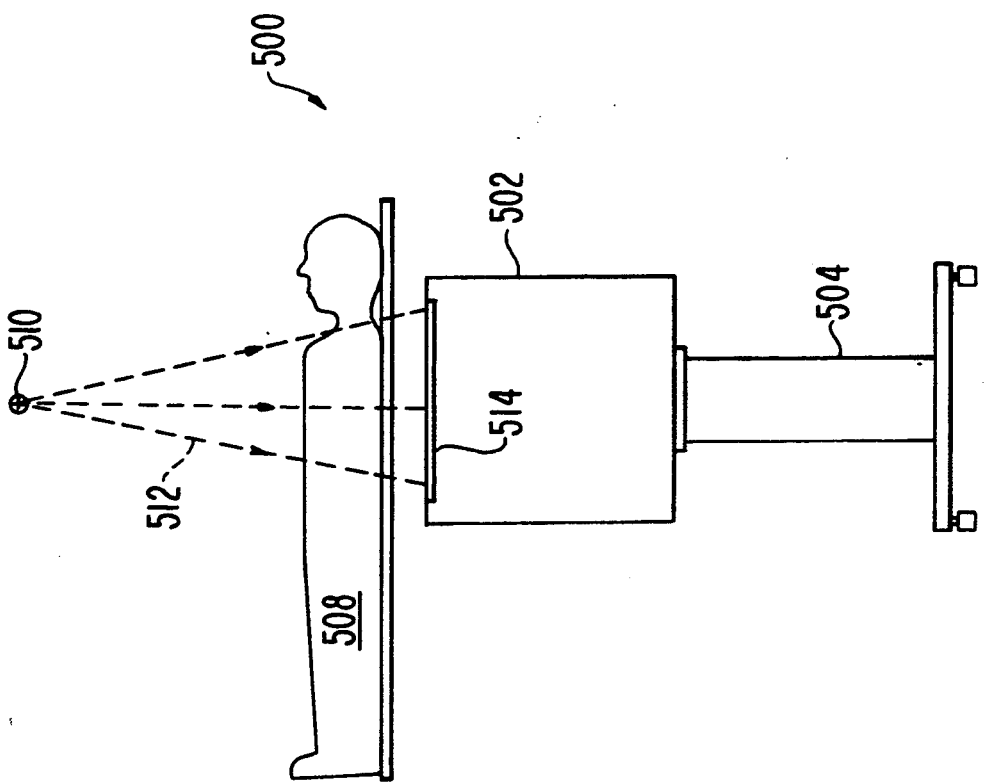
FIG. 13 is a front elevational view of the imaging system of FIG. 10 rotated one hundred and eighty degrees to be in a vertical imaging position.

As opposed to the single large bearing design of the rotation joint 24 of the embodiments of FIGS. 1-10 an improved arrangement is shown in the embodiment of FIGS. 10-14. In this embodiment, the rotation assembly 506 includes, as best depicted in FIG. 12, a rotatable shaft 530 secured at one end by an annular flange 532 to inside of the housing 502. The shaft 530 is rotatable within spaced bearings 534, 536 which are mounted to a plate 538 at the top of the stand 504. To balance the weight of the housing 502 and its internal components on the opposite side of the bearings and thereby to prevent the imaging system 500 from toppling, counterbalance weights 540 are secured to the opposite lower end of the shaft 530. This two small bearing design is less expensive than the previously-described single large bearing design.

To cover additional angles between orthogonal horizontal and vertical orientations of the housing 502, the housing can be rotated to any intermediate angle between them and releasably locked into place by any suitable locking device such as that previously described. The range of angles that can be covered is then from the vertically downward position to a horizontal position of the x-ray beam, or ninety degrees.

These x-ray radiation therapy machines (512) are mega voltage machines using high penetrating energy in the order of four to twenty MEVs. The imaging systems of this invention allow two orthogonal images to be shot to identify the location of the tumor in the patient 508. As opposed to the prior art method of using film in a cassette and moving the film behind the patient, processing the film and looking at the film through a viewer, the imaging systems herein allow for cost savings, quicker procedure and obviate the need for processing the film and save on storage. This is thus a very convenient system for changing the angle for modern therapy machines having isocentric motions. Additionally, mirror 518 facilitates the positioning of the imaging camera 520 out of the path of the x-rays passing through the screen 514. The thin mirror 518, which is in the order of two or three mils of stretched Mylar, for example, reduces the scattering of the radiation which causes bright spots to appear on the camera image thereby reducing the quality of the picture.

This invention is not to be construed as limited to the particular embodiments disclosed herein, since these are to be regarded as illustrative rather than restrictive. It is, therefore, to be understood that the invention may be practiced within the scope of the claims otherwise than as specifically described.

What is claimed is:

1. A multi-directional x-ray imager for use with an isocentric therapy x-ray machine having a rotatable x-ray source, said imager comprising:
    a fluorescence screen excitable by the projection thereon of x-rays from an x-ray source, which source is rotatable relative to the patient, of an isocentric therapy x-ray machine, to thereby emit light therefrom;
    an imaging means for imaging the emission of light from said fluorescence screen; and
    a forty-five degree rotational joint means for rotating and aligning said fluorescence screen relative to a different rotated position of the x-ray source relative to the patient.

2. The imager of claim 1 further comprising a housing having a window, said fluorescence screen being mounted at said window, and said rotational joint means rotating said housing.

3. The imager of claim 2 where said imaging means is positioned in said housing.

4. The imager of claim 2 further comprising said imaging means being out of the generally straight line path of x-rays from the source of x-rays passing through said fluorescence screen, and a mirror means attached to and rotatable with said housing for deflecting the light emitted from said fluorescence screen to said imaging means.

5. The imager of claim 2 wherein said imaging means comprises a video camera positioned in and rotatable with said housing.

6. The imager of claim 2 wherein said imaging means comprises a video camera positioned outside of said housing and fixed relative to the axis of rotation of said rotational joint means.

7. The imager of claim 2 wherein said rotational joint means comprises a bearing assembly having a rotation axis about which said housing is rotatable and a supporting means for supporting said bearing assembly.

8. The imager of claim 7 wherein said rotational joint means includes a counterbalance weight connected to the opposite side of said bearing assembly as said housing.

9. The imager of claim 8 wherein said counterbalance weight and said housing are on opposite sides of said supporting means.

10. The imager of claim 2 wherein said housing has a housing side defining a forty-five degree angle relative to the horizontal, and said rotational joint means is attached to said housing side and has its rotational axis extending therethrough.

11. The imager of claim 2 further comprising a hinge means for tilting said window and thereby said fluorescence screen out from said housing.

12. The imager of claim 2 wherein said rotational joint means comprises a rotatable shaft having a shaft first end secured to said housing and a shaft second end, a bearing assembly in which said shaft is rotatable, a support structure supporting said bearing assembly, and a counterbalance weight attached to said shaft second end.

13. The imager of claim 12 wherein said support structure includes a bearing mounting plate to which said bearing assembly is mounted and a base stand to which said bearing mounting plate is secured.

14. The imager of claim 12 wherein said housing has a housing opening and a housing surface adjacent thereto, said shaft first end passes through said housing opening, and said shaft first end has a radial shaft flange secured to said housing surface.

15. The imager of claim 1 wherein said fluorescence screen is rotatable by said rotational joint means between horizontal and vertical orientations and securable at any angle therebetween.

16. The imager of claim 1 wherein said imaging means is positioned out of the generally straight line path of x-rays from the source of x-rays passing through said fluorescence screen, and further comprising a deflecting mirror means for deflecting the light emitted from said fluorescence screen to said imaging means.

17. The imager of claim 16 wherein said mirror means comprises reflective material sheet means for preventing the scattering of x-rays from said deflecting mirror means to said imaging means.

18. The imager of claim 17 wherein said reflective material sheet means comprises a frame and a sheet of reflective material supported by and stretched onto said frame.

19. The imager of claim 18 wherein said reflective material comprises aluminized plastic.

20. The imager of claim 1 further comprising an upper box to which said fluorescence screen is mounted and a lower box supporting said rotational joint means.

21. The imager of claim 1 further comprising a generally upright stand on which said rotational joint means is mounted.

22. The imager of claim 1 wherein said rotational joint means comprises a U-section ring and a radial ring flange engaged in said U-section ring.

23. The imager of claim 1 further comprising a box to which said fluorescence screen is attached, said box having a box vertical axis, and said rotational joint means having its rotational axis disposed forty-five degrees relative to the box vertical axis.

24. The imager of claim 1 further comprising a video digitizer means for enhancing the video image from said imaging means.

25. The imager of claim 1 wherein said rotational joint means has a rotational axis, and said rotational joint means comprises a pair of bearings spaced along the rotational axis.

26. The imager of claim 1 further comprising a horizontally movable support stand on top of which said rotational joint means is mounted.

27. The imager of claim 26 further comprising a counterweight balance positioned outside of said stand and on the opposite side of said rotational joint means as said fluorescence screen.

28. The imager of claim 1 wherein said imaging means includes a charge-coupled-device camera.

29. The imager of claim 1 wherein said rotational joint means includes said different rotated position comprising an orthogonal position.

30. An imaging system for imaging a patient, said imaging system comprising:
   a fluorescence screen;
   a projecting means positionable on the opposite side of a patient from said fluorescence screen for projecting a beam of x-rays through said fluorescence screen and thereby exciting said fluorescence screen to emit light, said projecting means comprising an x-ray radiation therapy machine;
   an imaging means for imaging the emission of light from said fluorescence screen, said imaging means being sensitive to scattered x-rays and being located generally out of the straight line path of the x-rays from said projecting means passing through said fluorescence screen; and
   a deflecting mirror means for deflecting the light emitted from said fluorescence screen to said imaging means, said deflecting mirror means including a reflective material sheet means for preventing the scattering of x-rays from said deflecting mirror means to said imaging means.

31. The imaging system of claim 30 further comprising a light-tight housing having a window in which said fluorescence screen is mounted, and said deflecting mirror means being attached to said light-tight housing.

32. The imaging system of claim 31 wherein said imaging means is positioned outside of said light-tight housing.

33. The imaging system of claim 31 wherein said imaging means is positioned inside of said light-tight housing.

34. The imaging system of claim 30 wherein said imaging means comprises a solid-state video camera.

35. The imaging system of claim 30 wherein said reflective material sheet means comprises a frame and a sheet of reflective material supported by and stretched onto said frame.

36. The imaging system of claim 30 wherein said reflective material sheet means comprises a sheet of aluminized plastic.

37. The imaging system of claim 30 wherein said reflective material sheet means comprises a reflective sheet having a thickness of a tenth of a millimeter.

38. An imaging system comprising:
   (1) a repositionable x-ray source for imaging objects in a first direction and alternatively in a second direction orthogonal to the first direction; and
   (2) a bi-directional x-ray imager, said imager including:
      a fluorescence screen excitable by the projection thereon of x-rays from said x-ray source to thereby emit light therefrom;
      a video camera positioned to image the emissions of light from said fluorescence screen; and
      a rotational joint which rotates and aligns said fluorescence screen relative to the alternative first and second directions and about a rotation axis;
      wherein said video camera is disposed generally on the opposite side of the rotation axis as said fluorescence screen.

39. A multi-directional x-ray imager for use with an isocentric therapy x-ray machine having a rotatable x-ray source, said imager comprising:
   a fluorescence screen excitable by the projection thereon of x-rays from an x-ray source, which source is rotatable relative to the patient, of an isocentric therapy x-ray machine, to thereby emit light therefrom;
   an imaging means for imaging the emission of light from said fluorescence screen;
   a rotational joint means for rotating and aligning said fluorescence screen relative to a different rotated position of the x-ray source relative to the patient;
   a housing having a window at which said fluorescence screen is mounted;
   wherein said rotational joint means rotates said housing;
   wherein said imaging means is out of the generally straight line path of x-rays from the source of x-rays passing through said fluorescence screen; and
   a mirror means attached to and rotatable with said housing for deflecting the light emitted from said fluorescence screen to said imaging means.

40. A multi-directional x-ray imager for use with an isocentric therapy x-ray machine having a rotatable x-ray source, said imager comprising:
   a fluorescence screen excitable by the projection thereon of x-rays from an x-ray source, which source is rotatable relative to the patient, of an isocentric therapy x-ray machine, to thereby emit light therefrom;
   an imaging means for imaging the emission of light from said fluorescence screen;
   a rotational joint means for rotating and aligning said fluorescence screen relative to a different rotated position of the x-ray source relative to the patient; and a housing having a window at which said fluorescence screen is mounted;

wherein said rotational joint means rotates said housing;

wherein said housing has a housing side defining a forty-five degree angle relative to the horizontal; and wherein said rotational joint means is attached to said housing side and has its rotational axis extending therethrough.

41. A multi-directional x-ray imager for use with an isocentric therapy x-ray machine having a rotatable x-ray source, said imager comprising:

a fluorescence screen excitable by the projection thereon of x-rays from an x-ray source, which source is rotatable relative to the patient, of an isocentric therapy x-ray machine, to thereby emit light therefrom;

an imaging means for imaging the emission of light from said fluorescence screen;

a rotational joint means for rotating and aligning said fluorescence screen relative to a different rotated position of the x-ray source relative to the patient;

a housing having a window at which said fluorescence screen is mounted;

wherein said rotational joint means rotates said housing; and a hinge means for tilting said window and thereby said fluorescence screen out from said housing.

42. A multi-directional x-ray imager for use with an isocentric therapy x-ray machine having a rotatable x-ray source, said imager comprising:

a fluorescence screen excitable by the projection thereon of x-rays from an x-ray source, which source is rotatable relative to the patient, of an isocentric therapy x-ray machine, to thereby emit light therefrom;

an imaging means for imaging the emission of light from said fluorescence screen;

a rotational joint means for rotating and aligning said fluorescence screen relative to a different rotated position of the x-ray source relative to the patient; and a housing having a window at which said fluorescence screen is mounted;

wherein said rotational joint means rotates said housing; and wherein said rotational joint means comprises a rotatable shaft having a shaft first end secured to said housing and a shaft second end, a bearing assembly in which said shaft is rotatable, and a support structure supporting said bearing assembly.

43. The imager of claim 42 wherein said rotational joint means includes a counterbalance weight attached to said shaft second end.

44. The imager of claim 42 wherein said support structure includes a bearing mounting plate to which said bearing assembly is mounted and a base stand to which said bearing mounting plate is secured.

45. The imager of claim 42 wherein said housing has a housing opening and a housing surface adjacent thereto, said shaft first end passes through said housing opening, and said shaft first end has a radial shaft flange secured to said housing surface.

46. The imager of claim 42 wherein said imaging means comprises a video camera disposed generally on the opposite side of said rotatable shaft as said fluorescence screen.

47. A multi-directional x-ray imager for use with an isocentric therapy x-ray machine having a rotatable x-ray source, said imager comprising:

a fluorescence screen excitable by the projection thereon of x-rays from an x-ray source, which source is rotatable relative to the patient, of an isocentric therapy x-ray machine, to thereby emit light therefrom;

an imaging means for imaging the emission of light from said fluorescence screen;

a rotational joint means for rotating and aligning said fluorescence screen relative to a different rotated position of the x-ray source relative to the patient;

an upper box to which said fluorescence screen is mounted; and a lower box supporting said rotational joint means.

48. A multi-directional x-ray imager for use with an isocentric therapy x-ray machine having a rotatable x-ray source, said imager comprising:

a fluorescence screen excitable by the projection thereon of x-rays from an x-ray source, which source is rotatable relative to the patient, of an isocentric therapy x-ray machine, to thereby emit light therefrom;

an imaging means for imaging the emission of light from said fluorescence screen; and a rotational joint means for rotating and aligning said fluorescence screen relative to a different rotated position of the x-ray source relative to the patient;

wherein said rotational joint means comprises a U-section ring and a radial ring flange engaged in said U-section ring.

49. A multi-directional x-ray imager for use with an isocentric therapy x-ray machine having a rotatable x-ray source, said imager comprising:

a fluorescence screen excitable by the projection thereon of x-rays from an x-ray source, which source is rotatable relative to the patient, of an isocentric therapy x-ray machine, to thereby emit light therefrom;

an imaging means for imaging the emission of light from said fluorescence screen;

a rotational joint means for rotating and aligning said fluorescence screen relative to a different rotated position of the x-ray source relative to the patient; and a box to which said fluorescence screen is attached, said box having a box vertical axis;

wherein said rotational joint means has its rotational axis disposed forty-five degrees relative to the box vertical axis.

50. A multi-directional x-ray imager for use with an isocentric therapy x-ray machine having a rotatable x-ray source, said imager comprising:

a fluorescence screen excitable by the projection thereon of x-rays from an x-ray source, which source is rotatable relative to the patient, of an isocentric therapy x-ray machine, to thereby emit light therefrom;

an imaging means for imaging the emission of light from said fluorescence screen;

a rotational joint means for rotating and aligning said fluorescence screen relative to a different rotated position of the x-ray source relative to the patient;

a horizontally movable support stand on top of which said rotational joint means is mounted; and a counterweight balance positioned outside of said stand and on the opposite side of said rotational joint means as said fluorescence screen.

51. A multi-directional x-ray imager for use with an isocentric therapy x-ray machine having a rotatable x-ray source, said imager comprising:
a fluorescence screen excitable by the projection thereon of x-rays from an x-ray source, which source is rotatable relative to the patient, of an isocentric therapy x-ray machine, to thereby emit light therefrom;
an imaging means for imaging the emission of light from said fluorescence screen;
a rotational joint means for rotating and aligning said fluorescence screen relative to a different rotated position of the x-ray source relative to the patient; and
a housing having a window at which said fluorescence screen is mounted;
wherein said rotational joint means rotates said housing; and
wherein said rotational joint means comprises a bearing assembly having a rotation axis disposed at an angle relative to the horizontal and about which said housing is rotatable and a supporting means for supporting said bearing assembly.

52. The imager of claim 51 wherein said rotational joint means includes a counterbalance weight connected to the opposite side of said bearing assembly as said housing.

53. The imager of claim 52 wherein said counterbalance weight and said housing are on opposite sides of said supporting means.

54. The imager of claim 51 wherein said imaging means comprises a video camera disposed generally on the opposite side of the rotation axis as said fluorescence screen.

55. An imaging system comprising:
(1) an isocentric therapy x-ray machine having a rotatable x-ray source; and
(2) a multi-directional x-ray imager, said imager including:
a fluorescence screen excitable by the projection thereon of x-rays from said x-ray source, which source is rotatable relative to the patient, to thereby emit light therefrom;
imaging means for imaging the emission of light from said fluorescence screen;
a housing to which said fluorescence screen is mounted, said housing having a housing oblique surface; and
rotational joint means for rotating about a rotation axis and aligning said housing and thereby said fluorescence screen relative to a different rotated position of said x-ray source relative to the patient;
wherein the rotation axis passes through a central location of said housing oblique surface.

56. The imaging system of claim 55 wherein said rotational joint means has a rotational axis and a pair of bearings spaced along the rotational axis.

57. An imaging system comprising:
(1) an isocentric therapy x-ray machine having a rotatable x-ray source; and
(2) a multi-directional x-ray imager assembly, said imager assembly including:
a fluorescence screen excitable by the projection thereon of x-rays from said x-ray source, which source is rotatable relative to the patient, to thereby emit light therefrom;
an imager which images the emission of light from said fluorescence screen;
a housing to which said fluorescence screen is mounted; and
rotational joint means for rotating and aligning said fluorescence screen relative to a different rotated position of said x-ray source relative to the patient;
wherein said rotational joint means includes a rotation shaft having a shaft upper end; and
wherein said housing is mounted to and at said shaft upper end.

58. The imaging system of claim 57 wherein said rotational joint means has a pair of bearings spaced along said rotational shaft.

59. An imaging system comprising:
(1) a repositionable x-ray source for imaging objects in a first direction and alternatively in a second direction orthogonal to the first direction; and
(2) a bi-directional x-ray imager, said imager including:
a fluorescence screen excitable by the projection thereon of x-rays from said x-ray source to thereby emit light therefrom;
imaging means for imaging the emissions of light from said fluorescence screen; and
a forty-five degree rotational joint which rotates and aligns said fluorescence screen relative to the alternative first and second directions.

60. The imaging system of claim 59 wherein said rotational joint has a rotational axis and a pair of bearings spaced along the rotational axis.

61. A multi-directional x-ray imager for use with an isocentric therapy x-ray machine having a rotatable x-ray source, said imager comprising:
a fluorescence screen excitable by the projection thereon of x-rays from an x-ray source, which source is rotatable relative to a patient, of an isocentric therapy x-ray machine, to thereby emit light therefrom;
imaging means for imaging the emission of light from said fluorescence screen;
rotational joint means for rotating and aligning said fluorescence screen relative to a different rotated position of the x-ray source relative to the patient; and
a housing having a window at which said fluorescence screen is mounted;
wherein said rotational joint means rotates said housing;
wherein said rotational joint means comprises a bearing assembly having a rotation axis about which said housing is rotatable and a supporting means for supporting said bearing assembly;
wherein said rotational joint means includes a counterbalance weight connected to the opposite side of said bearing assembly as said housing; and
wherein said counterbalance weight and said housing are on opposite sides of said supporting means.

62. The imager of claim 61 wherein said imaging means comprises a video camera disposed generally on the opposite side of the rotation axis as said fluorescence screen.

* * * * *